US005686100A

United States Patent [19]
Wille et al.

[11] Patent Number: 5,686,100
[45] Date of Patent: Nov. 11, 1997

[54] PROPHYLACTIC AND THERAPEUTIC TREATMENT OF SKIN SENSITIZATION AND IRRITATION

[75] Inventors: John J. Wille, Trenton; Agis Kydonieus, Kendall Park, both of N.J.

[73] Assignee: E.R. Squibb & Sons, Inc., Princeton, N.J.

[21] Appl. No.: 545,244

[22] Filed: Oct. 19, 1995

Related U.S. Application Data

[63] Continuation-in-part of Ser. No. 343,156, Nov. 22, 1994, abandoned.

[51] Int. Cl.$^6$ ............................................. A61F 13/00
[52] U.S. Cl. ........................... 424/449; 424/447; 514/922; 514/944; 514/969
[58] Field of Search ..................... 424/449, 447; 514/944, 969, 922

[56] References Cited

U.S. PATENT DOCUMENTS

| 296,004 | 5/1884 | Asche | 24/63 |
|---|---|---|---|
| 4,556,560 | 12/1985 | Buckingham | 424/461 |
| 4,675,009 | 6/1987 | Hymes et al. | 604/304 |
| 4,885,154 | 12/1989 | Cormier et al. | 514/537 |
| 4,897,260 | 1/1990 | Ross et al. | 424/59 |
| 4,978,531 | 12/1990 | Yamazaki et al. | 424/448 |
| 5,000,956 | 3/1991 | Amkraut et al. | 424/434 |
| 5,008,110 | 4/1991 | Benecke et al. | 424/448 |
| 5,028,431 | 7/1991 | Franz et al. | 424/449 |
| 5,049,387 | 9/1991 | Amkraut | 424/435 |
| 5,077,054 | 12/1991 | Amkraut et al. | 424/486 |
| 5,118,509 | 6/1992 | Amkraut | 424/449 |
| 5,120,545 | 6/1992 | Ledger et al. | 424/449 |
| 5,130,139 | 7/1992 | Cormier et al. | 424/450 |
| 5,378,704 | 1/1995 | Weller | 514/80 |
| 5,451,407 | 9/1995 | Cormier et al. | 424/448 |

FOREIGN PATENT DOCUMENTS

90/09792 9/1990 WIPO.

OTHER PUBLICATIONS

Shah et al.; *Chemical Abstracts*, vol. 110, 1989, #121488.
Redrup, A.C. et al.; *Chemical Abstracts*, vol. 121, 1994, #1248766.
Moscato et al.; *Chemical Abstracts*, vol. 119, 1993, #173970.
Kydonieus et al.; *Chemical Abstracts*, vol. 121, 1994, #91918.
Richard L. Gallo, MD, PhD, Richard D. Granstein, MD, "Inhibition of Allergic Contact Dermatitis and Ultraviolet Radiation –Induced Tissue Swelling in the Mouse by Topical Amiloride", *Arch Dermatol*, vol. 125, Apr. 1989, pp. 502–506.
Alfred L. Goldberg & Kenneth L. Rock, "Proteolysis, proteasomes and antigen presentation", *Nature*, vol. 357, 4 Jun. 1992, pp. 375–379.
John McFadden, Kevin Bacon, and Richard Camp, "Topically Applied Verapamil Hydrochloride Inhibits Tuberculin-–Induced Delayed–Type Hypersensitivity Reactions in Human Skin", *The Journal of Investigative Dermatology*, vol. 99, No. 6, Dec. 1992, pp. 784–786.
Wolfgang Diezel et al., "Inhibition of Cutaneous Contact Hypersensitivity by Calcium Transport Inhibitors Lanthanum and Diltiazem", *The Journal of Investigative Dermatology*, vol. 93, No. 3, Sep. 1989, pp. 322–326.

*Primary Examiner*—D. Gabrielle Phelan
*Attorney, Agent, or Firm*—John M. Kilcoyne; Theodore R. Furman, Jr.

[57] ABSTRACT

Methods and devices for preventing and/or treating an adverse reaction of the skin to the presence of a skin-sensitizing and/or skin-irritating agent by administering an effective amount of a loop diuretic alone or in combination with at least one mast cell degranulator or at least one glucocorticosteroid.

27 Claims, No Drawings

PROPHYLACTIC AND THERAPEUTIC TREATMENT OF SKIN SENSITIZATION AND IRRITATION

RELATED APPLICATIONS

This is a Continuation-In-Part Application of U.S. Ser. No. 08/343,156 filed on Nov. 22, 1994, now abandoned.

FIELD OF THE INVENTION

The present invention relates to methods and compositions for preventing or treating adverse reactions of the skin to skin-sensitizing or skin-irritating agents.

BACKGROUND OF THE INVENTION

The skin is susceptible to penetration by agents that sensitize the skin or irritate the skin. As used herein the term "skin-sensitizing agent" is a substance that generally causes the formation of memory cells which recognize future contact with the sensitizing agent. Such future contact can result in an adverse reaction, both locally and at remote cites on the body. In general, a "skin-irritating agent" is a substance (e.g. soap) that causes an immediate and generally localized adverse response. The response is typically in the form of redness and/or inflammation and does not extend beyond the immediate area of contact nor does it cause the formation of memory cells. As used herein, the term "adverse skin reaction preventing or treating agent" shall mean collectively agents used in the present invention against skin-sensitizing agents and/or skin-irritating agents.

Allergic reactions of the skin to skin-sensitizing agents, known as allergic contact dermatitis (ACD), are immune responses that occur in the skin. The response is the result of the penetration of the skin by a foreign substance (e.g. hapten or antigen) that provokes a skin sensitization reaction. ACD is a two phase process involving an initial induction phase followed by an elicitation phase.

The induction phase occurs immediately after first time exposure of the skin to the hapten or antigen and is characterized by the formation of immune memory cells that can subsequently recognize the specific hapten or antigen which previously entered the skin for the first time.

The elicitation phase occurs when the skin is subsequently re-exposed to the original hapten or antigen. In the elicitation phase, the skin provides an overt reaction to the presence of the hapten or antigen in the form of a skin inflammatory response.

ACD generally results in a life-time persistent memory for the specific hapten or antigen. Thus, when the skin is exposed to the hapten or antigen at a subsequent time, there is typically an immediate and often severe skin inflammatory response.

Agents that cause allergic contact dermatitis are varied and numerous and include, for example, metals (e.g. nickel, chromium, cobalt and the like) fragrances, chemicals, cosmetics, textiles, pesticides, plastics, pollen and the like (see, for example, R. J. G. Rycroft et al. "Textbook of Contact Dermatitis"). Therapeutic agents such as drugs may also cause allergic contact dermatitis particularly when administered transdermally.

Transdermal delivery of drugs provides many advantages over alternate routes of administration. Transdermal delivery systems (TDS) for delivery of drugs or other beneficial agents are well-known (see, for example, U.S. Pat. Nos. 3,598,122, 3,598,123, 4,286,592, 4,314,557, 4,379,454, 4,599,222 and 4,573,995, which are each incorporated herein by reference). A TDS is generally composed of the following components: (a) "basic components", including backing, matrix reservoir, and an optional separate adhesive layer; (b) the drug or other therapeutic agent; (c) "additives", including solubilizers, plasticizers and permeation enhancers; and (d) "impurities" such as residual amounts of monomers, initiators, cross-linkers, etc., from the polymerization process during fabrication of the basic components.

The conditions under which TDS are administered are highly conducive to the induction of skin allergic reactions, and the following skin reactions may be expected to occur:

1. Irritant reactions to the drug, an additive, an impurity, or a combination thereof;
2. Allergic reactions, especially to the low molecular weight components (drug, additive, impurity, adhesive);
3. Local sweat retention syndrome resulting from prolonged skin occlusion which causes blocking of sweat ducts.

Allergic contact dermatitis presents a significant problem in the transdermal administration of therapeutic agents. It is well known that many drugs, including some currently marketed in the United States (e.g. clonidine) sensitize the skin when used in a transdermal delivery system. Skin sensitization may be produced not only by the transdermally delivered drug, but also by a non-sensitizing drug combined with skin sensitizing permeation enhancers, or a combination of a sensitizing drug and a sensitizing permeation enhancer. Penetration of these sensitizing agents into the skin and the resulting adverse reaction of the skin may persist well beyond the time that the transdermal patch is removed from the skin. The reaction of the skin may be a source of discomfort and a clinical complication in a patient suffering from such a reaction.

Unlike the response induced by skin-sensitizing agents, the non-allergic response to skin-irritating agents is immediate and localized and does not invoke activation of the immune system through the production of immune memory cells.

The most common response associated with skin-irritating agents is the onset of inflammation. The main steps of the inflammatory response include, the neurologic phase, the vascular phase and the cellular phase. In the neurologic phase transient vasoconstriction occurs typically within about 30 seconds of contact with the skin-irritating agent. Within about one to six minutes of contact, vasodilation occurs followed by the margination of neutrophils in the vessels and diapedesis, the outward passage of corpuscular elements through intact vessel walls.

The non-immune response to a skin-irritating agent is the result of a substance that causes direct toxic damage to the skin without preceding allergic sensitization. The response to contact is dependent upon the nature of the skin, the skin-irritating agent, its concentration, the situs of contact on the body and environmental factors such as humidity and temperature. Examples of potential skin-irritating agents include water, skin cleansers, industrial cleaning agents, alkalis, acids, oils, organic solvents, oxidizing agents, reducing agents, plant matter, animal matter, combinations thereof and the like.

Efforts have been made to address the problem of allergic contact dermatitis by prophylactically treating the skin to prevent the onset of the induction phase of ACD and/or to therapeutically prevent or reduce the adverse effects of the elicitation phase of ACD. For example, U.S. Pat. No. 5,202,130 discloses that lanthanide ions and organic calcium channel blockers individually can be used for the treatment of contact allergic dermatitis.

Wolfgang Diezel et al., *J. Invest. Derm.*, Vol. 93, No. 3, pp. 322–326 (Sep. 1989) discloses the sensitization of mice with 1-chloro-2, 4-dinitrobenzene and subsequent treatment with lanthanum citrate and diltiazem hydrochloride to prevent the onset of the induction phase of the sensitizing agent. Philip W. Ledger, et al., U.S. Pat. No. 5,120,545 disclose the prevention of skin sensitization by the administration of an antigen processing-inhibiting agent such as ammonium chloride. A method of preventing contact sensitization using steroids (e.g. corticosteroid and glucocorticoid carboxylic acid esters) is disclosed, for example, in Alfred Amkraut, U.S. Patent No. 5,118, 509 and Peter M. Ross, et al., U.S. Pat. No. 4,897,260.

A method of reducing the adverse effects of administering a sensitizing or irritating drug by using methyl nicotinate is disclosed in Michel Cormier et al., U.S. Patent No. 5,451, 407.

Methods of treating ACD through the blocking of the elicitation phase after initial exposure to a drug is disclosed, for example, in John McFadden, et al., *J. Invest. Derm.*, Vol. 99, No. 6, pp. 784–786 (Dec. 1992). Tuberculin-induced delayed-type hypersensitivity reaction in human skin was inhibited by topical application of verapamil hydrochloride prior to or concurrent with challenge with tuberculin.

Also, Richard L. Gallo, et al., *Arch. Dermatol.*, Vol. 125, pp. 502–506 (Apr. 1989) discloses the administration of the diuretic amiloride hydrochloride as a topical anti-inflammatory agent in the treatment of ACD, particularly mice sensitized with 2,4,6-trinitrobenzene.

As disclosed in commonly assigned U.S. Ser. No. 08/198, 003 filed Feb. 17, 1994, and references cited therein, irradiation of skin with ultraviolet light B (UVB) is known to be immunosuppressive. These UVB effects are thought to be mediated, in part, by the UVB-induced isomerization of trans-urocanic acid (trans-UCA), a molecule which makes up about 0.5% of the total dry weight in the upper layers of human epidermis, to cis-urocanic acid (cis-UCA). Cis-UCA is known to have various immunosuppressive actions in vivo in a number of experimental systems and is believed to act through histamine-like receptors in the skin. More recently, it has been shown that the UVB impairment of the induction phase of allergic contact dermatitis to epicutaneously applied haptens in certain mouse strains depended on the participation of the cytokine, tumor necrosis factor-a (TNFa). It has been suggested that local release of TNFa may inhibit sensitization by trapping epidermal Langerhans cells and preventing them from reaching the draining lymph node where they activate T. cells.

As further disclosed in U.S. Ser. No. 08/198,003, mast cell degranulators such as cis-urocanic acid are effective for preventing or inhibiting the skin sensitizing effect of a transdermally administered therapeutic agent.

Despite these efforts and the knowledge gained regarding the cause of ACD, there remains a need to develop compositions which effectively prevent the onset of ACD or reduce the adverse affects of ACD after the person has been sensitized to an agent, as for example, a transdermally administered agent such as a drug. There is likewise the need to develop compositions which effectively prevent reactions to skin-irritating agents.

Applicants have gained the knowledge that there is a distinct process step implicated in the immune response associated with allergic contact dermatitis, which when interfered with, results in the prevention and/or treatment of ACD. This process step referred to herein as cellular signal transduction, is believed responsible for the acquisition of memory by T-lymphocytes, for the cytokine-mediated regulation of antigen presentation and for other cellular processes as well.

Applicants have also discovered that a particular class of compounds having diuretic properties, referred to herein as high ceiling or loop diuretics alone or in combination with at least one mast cell degranulator or at least one glucocorticosteroid achieves significant improvement in the desensitization of a patient's skin and prevents and/or treats inflammation of the skin. As a result, the reaction of the skin to skin-sensitizing agents or skin-irritating agents is better controlled. The present invention therefore provides prevention and/or treatment of an adverse reaction to the skin, as well as a transdermal therapy which reduces discomfort to the patient.

SUMMARY OF THE INVENTION

The present invention is generally directed to methods of preventing or treating allergic contact dermatitis (ACD) and skin irritation and compounds and systems, especially transdermal systems, used in said methods. In one aspect of the invention a method is provided for preventing or treating an adverse reaction of the skin caused by the presence of skin-sensitizing agents such as therapeutic agents (e.g. drugs) metals, fragrances, cosmetics, textiles, pollen, pesticides, plastics, combinations thereof and the like, or skin-irritating agents such as cleansers, cleaning agents, alkalis, acids, oils and the like. The present invention is also applicable to ACD induced by the transdermal administration of an agent, as for example, a therapeutic agent such as a drug. In general, the present invention includes a method of preventing or treating an adverse reaction of the skin to the presence of at least one of a skin-sensitizing agent and skin-irritating agent comprising administering to a said warm-blooded animal an effective amount of an adverse skin preventing or treating agent comprising at least one loop diuretic alone or in combination with at least one mast cell degranulator or at least one glucocorticosteroid.

The skin-sensitizing or skin-irritating agents employed in the present invention can be prepared in the form of a composition containing one or more additives including skin permeation enhancers, excipients and the like.

These adverse skin reaction preventing or treating agents may be administered topically in the form of lotions, creams, sprays and the like, by non-cutaneous routes as well as through the use of transdermal patches. In transdermal applications, the agents may be administered from a single reservoir also containing a therapeutic agent or preferably from a separate reservoir of a transdermal patch.

DETAILED DESCRIPTION OF THE INVENTION

The present invention is in part directed to methods and systems for preventing the onset of skin sensitization reactions caused by allergic contact dermatitis by treatment before, after or during the induction phase of sensitization and for alleviating this condition once ACD has progressed to the elicitation phase. In one aspect of the invention the skin is treated with at least one high ceiling or loop diuretic alone or in combination with at least one mast cell degranulator or at least one glucocorticosteroid. The employment of a composition containing such adverse skin reaction preventing or treating agents provides desensitization of the skin to the presence of skin-sensitizing agents as encountered from a variety of sources including transdermal systems before, after or during the transdermal administration of the therapeutic agent.

Such adverse skin reaction preventing agents provide inhibition of the immune response and specific immune tolerance to the provoking antigen. More specifically, a single administration to the skin of a high ceiling or loop diuretic alone or in combination with at least one mast cell degranulator or at least one glucocorticosteroid renders a warm-blooded animal specifically unresponsive to an antigen, a state known as immunological tolerance. Three immunosuppressive agents known to induce immune tolerance are UVB radiation, the cytokine TNF-α and cis-urocanic acid. A number of mechanisms are thought to be responsible for the induction and maintenance of this tolerant state. Regardless of the mechanism, it is well-known that tolerance to an antigen which stimulates a sensitization response can be induced first by presenting the antigen in a tolerogenic form or via a tolerogenic route. The present invention encompasses a method wherein the immune response of an antigen is suppressed and a state of prolonged immunological tolerance is achieved.

High ceiling or loop diuretics of the type employed in the present invention affect signal transduction. In the renal tubule, these compounds interfere directly with the reabsorption and/or retention of potassium ions by blocking the action of the potassium ion channels in the Loop of Henle. It is believed that these compounds function as potassium ion pump poisons in that they indirectly interfere with the homeostatically regulated ion balance in other cells. The balance of hydrogen, sodium and calcium ions is upset by changing the net flux of intracellular potassium ions. Consequently, all those cellular processes dependent on the maintenance of homeostatically regulated intracellular ions are disrupted. In particular, the process of cellular signal transduction is known to be highly sensitive to changes in the level of intracellular ions, particularly potassium ions.

In another aspect of the present invention, the agents and compositions containing the same are also effective in preventing and/or treating adverse responses caused by skin-irritating agents such as household and industrial cleansers, organic solvents and the like. These agents are effective in disrupting the inflammatory response by limiting the ability of the skin-irritating agent to elicit the neurologic, vascular and/or cellular phase of inflammation.

Examples of loop diuretics for use in the present invention include ethacrynic acid, furosemide and bumetanide. Ethacrynic acid is the preferred loop diuretic.

The mast cell degranulating agents useful in the present invention are preferably selected from the group consisting of: cis-urocanic acid, or an analogue or a metabolite thereof, PUVA, chloroquine, histamine, capsaicin, morphine sulfate, a sodium channel ionophore, a calcium channel ionophore, an inhibitor of $Na^+/K^+$ channel ATPase, quinine, 4-aminopyridine, an anti-human IgE antibody, compound 48/80, substance P, estradiol, somatostatin, clonidine, progesterone, carbachol, and spantide. Some mast cell degranulating agents may, in appropriate concentrations, be therapeutic agents. Such agents include, for example capsaicin and clonidine.

Preferred cis-urocanic acid analogues for use in the present invention include, but are not limited to: (a) a cis or trans isomer of 1-furanacrylic acid; (b) a cis or trans isomer of 2-pyrrole acrylic acid; (c) a cis or trans isomer of 2-thiopheneacrylic acid; and (d) dihydrourocanic acid.

Preferred cis-urocanic acid metabolites for use in the present invention include, but are not limited to: (a) histamine; (b) $N^1$-methylhistamine; (c) $N^1$-methylhistidine; (d) histidine; (e) imidazolepyruvic acid; (f) $N^3$-methylhistidine; (g) imidazoleacetic acid; (h) hydantoin 5-propionic acid; and (i) imidazolonepropionic acid.

Glucocorticosteroids for use in the present invention include, for example, (a) hydrocortisone and analogs thereof, (b) beclomethasone, (c) betamethasone and analogs thereof, (d) clobetasol and analogs thereof, (e) desonide, (f) dexamethasone, (g) fluocinonide, (h) prednisone, and (i) triamcinolone. Hydrocortisone is the preferred gulcocorticosteroid.

The above methods are useful for preventing or treating skin sensitization or inflammation produced by a variety of skin-sensitizing agents such as, for example, a drug selected from, but not limited to, the following group: (a) an angiotensin converting enzyme inhibitor; (b) a beta adrenergic receptor blocker; (c) an anti-hypertensive drug other than an angiotensin converting enzyme inhibitor or a beta adrenergic receptor blocker; (d) an anti-histamine; (e) an anti-asthmatic; (f) a non-steroidal anti-inflammatory drug; (g) a central nervous system active drug; (h) a weight control drug; (i) an anticoagulant; (j) a potassium control drug; (k) an immunomodulatory drug; (l) a decongestant; and (m) proteins and peptides such as insulin and thyrotropin-releasing hormone.

More specifically, the therapeutic agents for administration in accordance with the present invention include all of the major therapeutic areas, including, but not limited to: anti-infectives, such as antibiotics and antivirals; analgesics and analgesic combinations (such as capsaicin); anorexics; antiarthritics; anti-asthmatics (such as albuterol, metaproterenol, ketotifen and terbutaline); anticoagulants (such as urokinase); anticonvulsants; antidepressants; antidiabetics; antidiarrheals; antihistamines (such as chlorpheniramine and diphenhydramine); anti-inflammatory agents (such as ketoprofen, prostaglandins, flurbiprofen, diclofenac, indomethacin, piroxicam and ibuprofen); antimigrane agents; anti-motion sickness preparations; antinauseants; antineoplastics; antiparkinsonism drugs; antipruritics; antipsychotics; antipyretics; antispasmodics, including gastrointestinal and urinary; anticholinergics; sympathomimetics; xanthine derivatives; cardiovascular agents, including angiotensin converting enzyme inhibitors (such as captropril and fosinopril); beta blockers (such as nadolol, timolol, propranolol and alprenolol); antiarrythmics; antihypertensives (such as clonidine); vasodilators, including general, coronary, peripheral and cerebral; central nervous acting agents (such as fluphenazine, trifluoperazine, haloperidol, Xanax®, Librium®, Valium®); cough and cold preparations; decongestants; diagnostics; hormones; hypnotics; muscle relaxants; parasympatholytics; parasympathomimetics; psychostimulants; sedatives; weight control and appetite suppressive drugs (such as mazindol) and tranquilizers.

The above methods are also useful for preventing or treating skin irritation produced by a variety of skin-irritating agents as previously described including but not limited to household and industrial cleansers, water, organic solvents, oxidizing and/or reducing agents, alkalis, acids, oils, plant matter, animal matter and the like.

The present invention further provides an article useful for preventing or treating the skin sensitizing or inflammatory effect of a component of a transdermal drug delivery system, where the component is either a drug, a skin permeation enhancer or a combination of the two and the like, the article comprising:

(a) a transdermal delivery system comprising a therapeutic agent (e.g. a drug) of interest; and
(b) an effective amount of at least one high ceiling or loop diuretic alone or in combination with at least one mast cell degranulator or at least one glucocorticosteroid.

The adverse skin reaction preventing or treating agents can also be administered in a transdermal or a controlled-release device. Examples of transdermal devices and delivery systems which may be used are disclosed in Bodde, H. E. et al., Crit. Rev. Ther. Drug Carrier Syst. 6:87–115 (1989); and in U.S. Pat. Nos. 3,598,122, 3,598,123, 4,286,592, 4,314,557, 4,379,454, 4,559,222, 4,573,995, which references are hereby incorporated by reference.

The delivery system may include a first transdermal device comprising a matrix for placing the adverse skin reaction preventing or treating agents in transmitting relationship to the skin. A second transdermal device may be used to place the therapeutic agent in transmitting relationship to the skin after the adverse reaction preventing or treating agent has been transdermally administered to the skin. The first and second transdermal devices may be incorporated into a single transdermal patch.

The adverse skin reaction preventing or treating agents are administered by themselves or, in transdermal systems in combination with a therapeutic agent of interest. These agents may be administered topically or non-cutaneously such as intradermally, intravenously, intramuscularly, orally or intraperitoneally. The agents of the present invention can be incorporated into a pharmaceutically acceptable composition for topical application to the skin in the form of lotions, creams gels and the like. Useful carriers for the preparations of such compositions include water, ethanol, gels and the like.

The precise formulation of the transdermally administered therapeutic agent (e.g. a drug) and the adverse skin reaction preventing or treating agents of the present invention can be designed to deliver the drug and the agents at the desired fluxes and can be in numerous forms, including, without limitation, ointments, gels and creams. Aqueous formulations, in particular gels, typically comprise water and from about 1 to 2.5% (w/w) of a gelling agent such as hydroxyethylcellulose or hydroxypropylmethylcellulose (HPMC). Typical non-aqueous gels comprise silicone fluid or mineral oil. The mineral oil may also have from about 1 to 2% (w/w) of a gelling agent such as colloidal silicon dioxide. The suitability of a particular gel composition depends on the compatibility of its constituents with the drug (with or without a permeation enhancer) and the adverse skin reaction preventing or treating agents.

In another embodiment, the agents of the present invention are delivered to the skin alone to prevent skin-sensitization and/or skin irritation or prior to the administration of the therapeutic drug or drugs. Such prior administration can be via transdermal application using a device as described above, via topical application, intracutaneous injection, and the like.

In yet another embodiment, the agents are delivered by another non-cutaneous route and method of delivery, either concurrently with, or prior to, the transdermal administration of the therapeutic drug.

In embodiments of the invention where the adverse skin reaction preventing or treating is administered to prevent or treat irritation of the skin, the composition containing the same is preferably in the form of a lotion, cream or other readily applied topical formulation.

In all of the above embodiments, the dosage of the adverse skin reaction preventing or treating agents administered will be dependent upon the agent, the age, health, and weight of the recipient, kind of concurrent treatment, if any, and frequency of treatment.

The methods and compositions within the scope of this invention include all compositions and methods wherein the adverse skin reaction preventing or treating agents are contained in an amount effective to achieve their intended purpose. While individual needs vary, determination of optimal ranges of effective amounts of each component is within the skill of the art.

For transdermal administration, typical effective dosages of the agents to prevent and/or treat ACD by a sensitizing drug will depend on their permeation through human skin, and are a function of the physical properties of the permeant, including the partition coefficient of the permeant between solvent and skin, molecular weight and melting point. In general, the maximum flux that can be obtained from any permeant occurs from saturated solutions. Equations have been derived that predict accurately the maximum flux given the partition coefficient, molecular weight and melting point of the permeant as described in, for example, "TREATISE ON CONTROLLED DRUG DELIVERY", A. Kydonieus, ed., Marcel Dekker, Inc., New York, 1991, in particular, p. 370, equations 3a and 4a and p. 34, FIG. 2, incorporated herein by reference. For example, for the transdermal delivery of the loop diuretics alone or in combination with the mast cell degranulators including the preferred agents, ethacrynic acid and cis-urocanic acid, the expected maximum flux that can be delivered locally to skin is in the range of from about 1 to 50 $\mu g/cm^2/hr$. For transdermal delivery of glucocorticosteroids, including the preferred agent hydrocortisone, the expected maximum flux that can be delivered locally to the skin is in the range of from about 0.005 to 5 $\mu g/cm^2/hr$.

These values are dependent, for example on varying skin age, skin type and skin condition. The preferred range for the maximum flux for ethacrynic acid plus cis-urocanic acid is from about 5 to 25 $\mu g/cm^2/hr$. For the administration of hydrocortisone the preferred range for the maximum flux is from about 0.01 to 1.0 $\mu g/cm^2/hr$. Accordingly, as will be understood by those skilled in the art, the delivery of a particular agent, is controlled by the percent saturation of that agent in the chosen vehicle.

The amount of the loop diuretic agent, mast degranulator or glucocorticosteroid which can be delivered to prevent or treat ACD will vary from patient to patient. For example, the amount of the loop diuretic (e.g. ethacrynic acid) delivered from a gel formulation (2.5% HPMC in 75% ethanol) is from about 0.1 to 10% by weight, and preferably from about 0.25% to 2.0% by weight. The amount of the mast cell degranulator (e.g. cis-urocanic acid), which is preferably employed from the same gel formulation in the present invention is in the range of from about 0.1 to 20% by weight, preferably from about 1 to 10% by weight. The amount of glucocorticosteroid (e.g. hydrocortisone) which is preferably employed from the same gel formulation in the present invention is in the range of from about 0.05% to 5% by weight.

For administration of the adverse skin reaction preventing agents to prevent or treat skin irritation, the dosage will vary as described. For example for topical application, the preferred agents are loop diuretics alone (e.g. ethacrynic acid) or in combination with a mast cell degranulator (e.g. cis-urocanic acid). In general, the amount of the loop diuretic (e.g. ethacrynic acid) is from about 0.1 to 2.0 percent by weight, preferably from about 0.25 to 1.0 percent by weight based on the total weight of the composition.

The amount of the mast cell degranulator (e.g. cis-urocanic acid) is typically from about 1.0 to 20 percent by weight, preferably from about 2.0 to 10 percent by weight based on the total weight of the composition.

The amount of glucocorticosteroid for prevention or treatment of skin irritation is from about 0.1 to 5.0 percent by weight, preferably from about 0.5 to 2.0 percent by weight.

EXAMPLE 1

Ethacrynic Acid as A Counter Sensitizer to DNCB

A 0.5% (w/v) solution of ethacrynic acid was prepared in a gel formulation (2.5% HPMC in 75% ethanol). The same gel formulation served as a negative control. For sensitization, a 1% (w/v) solution of dinitrochlorobenzene (DNCB) was prepared in acetone.

Twenty-four (24) Balb/c mice had their abdominal skin shaved. The mice were divided into three equal groups. The first group acted as a negative control and received on day 0 an application of 0.2 mL of hydroxypropylmethylcellulose (HPMC) on their exposed their exposed abdominal skin. The second group acted as a positive control by receiving on day 0, 0.2 mL of HPMC gel on exposed abdominal skin. The third group of mice was treated with 0.2 mL of HPMC gel containing ethacrynic acid on day 0.

Twenty-four (24) hours later, the mice in Groups II and III received 10 µL of 1% DNCB solution over the skin area pretreated with gel, while the mice in Group I received 10 µL of acetone. All three groups were challenged on the right ear with 20 µL of 1% DNCB in acetone five (5) days after sensitization.

Adverse reaction to the challenge with DNCB was determined by measuring the thickness of the mice ears before and after challenge to determine the amount of swelling, and then comparing the degree of swelling for mice treated in accordance with the invention (Group III) with Groups I and Groups II. The results are shown in Table I.

TABLE I

| TREATMENT | EAR THICKNESS (MM × $10^{-3}$) | EAR SWELLING (MM × $10^{-3}$) | % SUPPRESSION |
|---|---|---|---|
| GROUP I NONE (HPMC GEL) | | | |
| 24 HOURS | 238 ± 5 | — | — |
| 48 HOURS | 243 ± 7 | — | — |
| GROUP II DNCB ONLY (100 µg) | | | |
| 24 HOURS | 318 ± 33 | 80.0 | — |
| 48 HOURS | 312 ± 22 | 69.0 | — |
| GROUP III ETHACRYNIC ACID 1 MG (IN HPMC GEL) (PRE ONLY) + DNCB (100 µg) | | | |
| 24 HOURS | 281 ± 26 | 42 | 50 |
| 48 HOURS | 282 ± 17 | 39 | 47 |

As shown in Table I, the Group II mice exhibited significant ear swelling when sensitized to DNCB. The loop diuretic, ethacrynic acid alone constituting an adverse skin reaction preventing agent when administered prophylactically limits adverse reactions induced by sensitization with DNCB.

EXAMPLE 2

Furosemide as A Counter Sensitizer to DNCB

The procedures of Example 1 were repeated except that the adverse skin reaction preventing or treating agent was a 1.0% (w/v) formulation of furosemide. The results are shown in Table II.

TABLE II

| TREATMENT | EAR THICKNESS (MM × $10^{-3}$) | EAR SWELLING (MM × $10^{-3}$) | % SUPPRESSION |
|---|---|---|---|
| GROUP I NONE (HPMC GEL) | | | |
| 24 HOURS | 236 ± 4 | — | — |
| GROUP II DNCB ONLY (100 µg) | | | |
| 24 HOURS | 299 ± 35 | 63 | — |
| GROUP III FUROSEMIDE 2 MG (IN HPMC GEL) + DNCB (100 µg) | | | |
| 24 HOURS | 288 ± 18 | 52 | 17 |

As shown in Table II, the Group II mice exhibited significant ear swelling when sensitized to DNCB. Furosemide constituting an adverse skin reaction preventing agent when administered prophylactically limits adverse skin reactions induced by sensitization to DNCB.

EXAMPLE 3

Ethacrynic and Cis Urocanic Acid as Counter Sensitizers to DNCB

The procedures of Example 1 were repeated except that the adverse skin reaction preventing or treating agent was a combination of a 2.5% (w/v) solution of cis-urocanic acid and a 0.25% (w/v) of ethacrynic acid solution prepared in the above HPMC gel. The results are shown in Table III.

TABLE III

| TREATMENT | EAR THICKNESS (MM × $10^{-3}$) | EAR SWELLING (MM × $10^{-3}$) | % SUPPRESSION |
|---|---|---|---|
| GROUP I (HPMC GEL) | | | |
| 24 HOURS | 241 ± 4 | — | — |
| 48 HOURS | 243 ± 5 | — | — |
| GROUP II DNCB ONLY (100 µg) | | | |
| 24 HOURS | 318 ± 24 | 77.0 | — |
| 48 HOURS | 326 ± 23 | 83.0 | — |
| GROUP III (CIS UROCANIC ACID 10 MG + ETHACRYNIC ACID 1 MG IN HPMC GEL) (PRE ONLY) + DNCB (100 µg) | | | |
| 24 HOURS | 245 ± 13 | 4 | 95 |
| 48 HOURS | 264 ± 23 | 21 | 74 |

As shown in Table III, the Group II mice exhibited significant ear swelling when sensitized with DNCB. The combination of cis-urocanic acid and ethacrynic acid constituting an adverse skin reaction preventing or treating agent in accordance with the present invention suppressed adverse reactions induced by sensitization with DNCB.

EXAMPLE 4

Ethacrynic Acid and Hydrocortisone as Counter Sensitizers to DNCB

The procedures of Example 1 were repeated except that the adverse skin reaction preventing or treating agent was a combination of a 1% (w/v) solution of hydrocortisone, and a 0.25% (w/v) solution of ethacrynic acid, prepared in the above gel formulation. The results are shown in Table IV.

TABLE IV

| TREATMENT | EAR THICKNESS (MM × $10^{-3}$) | EAR SWELLING (MM × $10^{-3}$) | % SUPPRESSION |
|---|---|---|---|
| NONE (HPMC GEL) | | | |
| 24 HOURS | 250 ± 5 | — | — |
| 48 HOURS | 245 ± 7 | — | — |
| DNCB ONLY (100 µg) | | | |
| 24 HOURS | 371 ± 21 | 121 | — |
| 48 HOURS | 371 ± 30 | 126 | — |
| (Hydrocortisone 2 mg + Ethacrynic Acid 0.5 mg) (in HPMC GEL) (PRE ONLY) + DNCB (100 µg) | | | |
| 24 HOURS | 318 ± 42 | 68 | 44.1 |
| 48 HOURS | 293 ± 26 | 48 | 62.1 |

As shown in Table IV, the Group II mice showed significant ear swelling when sensitized with DNCB. The combination of hydrocortisone and ethacrynic acid constituting an adverse skin reaction preventing or treating agent in accordance with the present invention suppressed adverse reactions induced by sensitization with DNCB.

EXAMPLE 5

Ethacrynic Acid as A Counter Sensitizer to Albuterol

Forty (40) CBA/J female mice were obtained from Jackson Labs. A 0.5% (w/v) solution of ethacrynic acid was prepared in a gel formulation (2.5% HPMC in 75% ethanol). A 5% (w/v) solution and a 1% (w/v) solution of albuterol were also prepared. In addition a 2.5% HPMC solution was prepared as a placebo.

The mice were shaved on their back. Positive control mice (10) received the placebo and the 5% albuterol solution on alternating days for three weeks. The experimental mice (10) received the ethacrynic acid solution and the 5% albuterol solution on alternating days for three weeks.

A negative control group of mice (20) received the placebo gel on each day for three weeks.

Five days after the last application each group of mice were challenged on the right ear with the 1% albuterol solution and on the left ear with the placebo gel. The thickness of the ears was measured after 24, 48, and 72 hours. The results are shown in Table V.

TABLE V

| TREATMENT | EAR SWELLING (MM × $10^{-3}$) | % SUPPRESSION |
|---|---|---|
| GROUP 1 NONE (HPMC GEL) | | |
| 24 HOURS | — | — |
| 48 HOURS | — | — |
| 72 HOURS | — | — |
| GROUP II ALBUTEROL ONLY | | |
| 24 HOURS | 52 | — |
| 48 HOURS | 83 | — |
| 72 HOURS | 57 | — |
| GROUP III ETHACRYNIC ACID + ALBUTEROL | | |
| 24 HOURS | 0 | 100 |
| 48 HOURS | 0 | 100 |
| 72 HOURS | 17 | 79 |

As shown in Table V, the Group II mice exhibited significant ear swelling when sensitized to albuterol. Ethacrynic acid alone constituting an adverse skin reaction preventing or treating agent limited adverse reactions induced by sensitization with albuterol.

EXAMPLE 6

Ethacrynic Acid as A Counter Sensitizer to Chlorpheniramine

The procedures of Example 5 were repeated except that the mice were sensitized with chlorpheniramine in an amount of 5% (w/v). The results are shown in Table VI.

TABLE VI

| TREATMENT | EAR SWELLING (MM × $10^{-3}$) | % SUPPRESSION |
|---|---|---|
| GROUP I NONE (HPMC GEL) | | |
| 24 HOURS | — | — |
| 48 HOURS | — | — |
| 72 HOURS | — | — |
| GROUP II CHLORPHENIRAMINE ONLY | | |
| 24 HOURS | 56 | — |
| 48 HOURS | 53 | — |
| 72 HOURS | 28 | — |
| GROUP III ETHACRYNIC ACID + CHLORPHENIRAMINE | | |
| 24 HOURS | 0 | 100 |
| 48 HOURS | 0 | 100 |
| 72 HOURS | 0 | 100 |

As shown in Table VI, the Group II mice exhibited significant ear swelling when sensitized to chlorpheniramine. Ethacrynic acid alone constituting an adverse skin reaction preventing or treating agent limited adverse reactions induced by sensitization with chlorpheniramine.

EXAMPLE 7

Ethacrynic Acid as A Counter Sensitizer to Clonidine

The procedures of Example 5 were repeated except that the mice were sensitized with clonidine in an amount of 5% (w/v). The results are shown in Table VII.

татя VII

| TREATMENT | EAR SWELLING (MM × 10⁻³) | % SUPPRESSION |
|---|---|---|
| GROUP I NONE (HPMC GEL) | | |
| 24 HOURS | — | — |
| 48 HOURS | — | — |
| 72 HOURS | — | — |
| GROUP II CLONIDINE ONLY | | |
| 24 HOURS | 32 | — |
| 48 HOURS | 52 | — |
| 72 HOURS | 22 | — |
| GROUP III ETHACRYNIC ACID + CLONIDINE | | |
| 24 HOURS | 0 | 100 |
| 48 HOURS | 0 | 100 |
| 72 HOURS | 7 | 67 |

As shown in Table VII, the Group II mice exhibited significant ear swelling when sensitized to clonidine. Ethacrynic acid alone constituting an adverse skin reaction preventing or treating agent limited adverse reactions induced by sensitization with clonidine.

EXAMPLE 8

Ethacrynic Acid as A Counter Sensitizer to Nadolol

The procedures of Example 5 were repeated except that the skin sensitizing agent was nadolol in an amount of 5% (w/v). The results are shown in Table VIII.

TABLE VIII

| TREATMENT | EAR SWELLING (MM × 10⁻³) | % SUPPRESSION |
|---|---|---|
| GROUP I NONE (HPMC GEL) | | |
| 24 HOURS | — | — |
| 48 HOURS | — | — |
| 72 HOURS | — | — |
| GROUP II NADOLOL ONLY | | |
| 24 HOURS | 52 | — |
| 48 HOURS | 53 | — |
| 72 HOURS | 63 | — |
| GROUP III ETHACRYNIC ACID + NADOLOL | | |
| 24 HOURS | 0 | 100 |
| 48 HOURS | 0 | 100 |
| 72 HOURS | 20 | 67 |

As shown in Table VIII, the Group II mice exhibited significant ear swelling when sensitized to nadolol. Ethacrynic acid alone constituting an adverse skin reaction preventing or treating agent limited adverse reactions induced by sensitization with nadolol.

EXAMPLE 9

Ethacrynic Acid as A Counter Sensitizer to Mice Already Sensitized to Oxazolone

In this example, the question was considered as to whether ethacrynic acid could prevent an adverse reaction after the mice were sensitized by a primary exposure to oxazolone and then treated immediately after challenge with the sensitizing agent.

Thirty (30) Balb/c female mice were obtained from Sprague Dawley Labs. A 1.0% (w/v) solution of ethacrynic acid was prepared in a gel formulation (1.0% HPMC in 75% ethanol). A 1% (w/v) solution of oxazolone in acetone was also prepared. In addition a 1.0% HPMC solution was prepared as a placebo.

The mice were shaved on their back and divided into three groups. Group II (10 mice) acted as a positive control and received 10 μL of the oxazolone solution. Group III (10 mice) were designated the experimental mice and received 10 μL of the oxazolone solution. Group I (10 mice) acted as a negative control group and received 10 μL of acetone.

Five days after the last application, Groups I, II and III mice received 20 μL of the oxazolone solution to the right ear. Five minutes after the challenge, 100 μL of the placebo was applied to the right ears of Groups I and II and 100 μL of the ethacrynic acid solution was applied to the right ears of the Group III mice. The thickness of the ears was measured after 24 and 48 hours. The results are shown in Table IX.

TABLE IX

| TREATMENT | EAR SWELLING (MM × 10⁻³) | % SUPPRESSION |
|---|---|---|
| GROUP I NONE (HPMC GEL) | | |
| 24 HOURS | — | — |
| 48 HOURS | — | — |
| GROUP II OXAZOLONE ONLY | | |
| 24 HOURS | 119 | — |
| 48 HOURS | 130 | — |
| GROUP III ETHACRYNIC ACID + OXAZOLONE | | |
| 24 HOURS | 47 | 61 |
| 48 HOURS | 87 | 33 |

As shown in Table IX, the Group II mice exhibited significant ear swelling when sensitized to oxazolone. Ethacrynic acid alone constituting an adverse skin reaction preventing or treating agent limited adverse reactions after mice were already sensitized with oxazolone.

EXAMPLE 10

Ethacrynic Acid Inhibits Irritation Induced by Lactic Acid

Thirty (30) Balb/c female mice were obtained from Sprague Dawley Labs. A 1.0% (w/v) solution of ethacrynic acid was prepared in a gel formulation (2.5% HPMC in 75% ethanol). A 25% (w/v) solution of lactic acid (sufficient to elicit a strong irritant response), was also prepared. In addition a 1.0% HPMC solution was prepared as a placebo.

The mice were shaved on their back. Group I (10 mice) received the placebo only. Positive control mice (10) designated as Group II received the lactic acid solution to the right ear and five minutes later 50–100 μL of the placebo. The experimental mice (10) (Group III) received the ethacrynic acid solution to the right ear followed five minutes later by the lactic acid solution.

The thickness of the ears was measured after 2 hours when maximum redness and swelling from lactic acid were observed. The results are shown in Table X.

TABLE X

| TREATMENT | EAR THICKNESS (MM × 10⁻³) | % SUPPRESSION |
|---|---|---|
| GROUP I NONE (HPMC GEL) | | |
| 2 HOURS | 240 ± 9 | — |
| GROUP II LACTIC ACID ONLY | | |
| 2 HOURS | 276 ± 23 | — |
| GROUP III ETHACRYNIC ACID + LACTIC ACID | | |
| 2 HOURS | 243 ± 12 | 99 |

As shown in Table X, the Group II mice exhibited significant ear swelling when contacted with lactic acid. Ethacrynic acid constituting an adverse skin reaction preventing or treating agent suppressed inflammation induced by contact with lactic acid.

EXAMPLE 11

Ethacrynic Acid Inhibits Irritation Induced by Capsaicin

The procedures of Example 10 were repeated except that lactic acid was replaced by capsaicin in an amount of 5% (w/v) in a 1% HPMC gel. The results are shown in Table XI.

TABLE XI

| TREATMENT | EAR THICKNESS (MM × 10⁻³) | % SUPPRESSION |
|---|---|---|
| GROUP I NONE (HPMC GEL) | | |
| 2 HOURS | 269 ± 11 | — |
| GROUP II CAPSAICIN ONLY | | |
| 2 HOURS | 338 ± 23 | — |
| GROUP III ETHACRYNIC ACID + CAPSAICIN | | |
| 2 HOURS | 298 ± 19 | 58.6 |

As shown in Table XI, the Group II mice exhibited significant ear swelling when contacted with capsaicin. Ethacrynic acid constituting an adverse skin reaction preventing or treating agent suppressed inflammation induced by capsaicin.

EXAMPLE 12

Ethacrynic Acid Inhibits Irritation Induced By Arachidonic Acid

The procedures of Example 10 were repeated except that lactic acid was replaced with arachidonic acid in an amount of 5% (w/v) in a 1% HPMC gel. The results are shown in Table XII.

TABLE XII

| TREATMENT | EAR THICKNESS (MM × 10⁻³) | % SUPPRESSION |
|---|---|---|
| GROUP I NONE (HPMC GEL) | | |
| 2 HOURS | 241 ± 9 | — |
| GROUP II ARACHIDONIC ACID ONLY | | |
| 2 HOURS | 327 ± 13 | — |
| GROUP III ETHACRYNIC ACID + ARACHIDONIC ACID | | |
| 2 HOURS | 289 ± 22 | 45 |

As shown in Table XII, the Group II mice exhibited significant ear swelling when contacted with arachidonic acid. Ethacrynic acid constituting an adverse skin reaction preventing or treating agent suppressed inflammation induced by contact with arachidonic acid.

EXAMPLE 13

Ethacrynic Acid Inhibits Irritation Induced By PMA

The procedures of Example 10 were repeated except that lactic acid was replaced with phorbol 12-myristate 13-acetate (PMA) in an amount of 0.1% (w/v) in a 1% HPMC gel. The results are shown in Table XIII.

TABLE XIII

| TREATMENT | EAR THICKNESS (MM × 10⁻³) | % SUPPRESSION |
|---|---|---|
| GROUP I NONE (HPMC GEL) | | |
| 2 HOURS | 226 ± 4 | — |
| GROUP II PMA ONLY | | |
| 2 HOURS | 265 ± 14 | — |
| GROUP III ETHACRYNIC ACID + PMA | | |
| 2 HOURS | 226 ± 9 | 100 |

As shown in Table XIII, the Group II mice exhibited significant ear swelling when contacted with phorbol 12-myristate 13-acetate. Ethacrynic acid constituting an adverse skin reaction preventing or treating agent suppressed inflammation induced by contact with PMA.

What is claimed is:

1. A method of preventing or treating an adverse reaction of the skin of a warm-blooded animal to the presence of at least one of a skin-sensitizing agent or a skin-irritating agent comprising topically administering to said warm-blooded animal an amount of an adverse skin reaction preventing or treating agent sufficient to prevent or treat said adverse reaction without achieving a systemically active concentration, said adverse skin reaction preventing or treating agent comprising at least one loop diuretic alone or in combination with at least one mast cell degranulator or glucocorticosteroid.

2. The method of claim 1 wherein the skin-sensitizing agent is selected from the group consisting of therapeutic agents, metals, fragrances, cosmetics, textiles, pollen, pesticides, plastics and combinations thereof.

3. The method of claim 1 wherein the skin-irritating agent is selected from the group consisting of water, cleansers, alkalis, acids, oils, organic solvent, oxidizing agents, reducing agents, and combinations thereof.

4. The method of claim 1 where said adverse skin reaction preventing or treating agent is administered transdermally.

5. The method of claim 4 wherein the skin-sensitizing agent is a therapeutic agent, said method comprising administering said adverse skin reaction preventing or treating agent and the therapeutic agent from a transdermal patch.

6. The method of claim 1 wherein the loop diuretic is selected from the group consisting of ethacrynic acid, furosemide and bumetanide.

7. The method of claim 6 wherein the loop diuretic is ethacrynic acid.

8. The method of claim 1 wherein the mast cell degranulator is selected from the group consisting of cis-urocanic acid, 1-furanacrylic acid, 2-pyrole acrylic acid, 2-thiophenacrylic acid, dihydrourocanic acid, trans-urocanic acid, histamine, $N^1$-methylhistamine, $N^1$-methyl histidine, histidine, imidazolepyruvic acid, $N^3$-methylhistidine, imidazoleacetic acid, hydantoin 5-propionic acid, imidazolonepropionic acid, psoralen treated with ultraviolet radiation, chloroquine, histamine, capsaicin, morphine sulfate, a sodium channel ionophore, a calcium channel ionophore, an inhibitor of Na+/K+channel ATPase, quinine, 4-amino pyridine, anti-human IgE antibody, substance P, estradiol, somatastatin, carbachol, progesterone, spantide, and clonidine.

9. The method of claim 1 wherein the analogs of cis-urocanic acid are selected from the group consisting of 1-furanacrylic acid, 2-pyrole acrylic acid, 2-thiophenacrylic acid, dihydrourocanic acid and trans-urocanic acid.

10. The method of claim 8 wherein the mast cell degranulator is cis-urocanic acid.

11. The method of claim 1 wherein the glucocorticosteroid is selected from the group consisting of hydrocortisone, beclomethasone, betamethasone, clobetasol, desonide, dexamethasone, fluocinonide, prednisone, and triamcinolone.

12. The method of claim 11 wherein the glucocorticosteroid is hydrocortisone.

13. The method of claim 4 wherein the maximum flux of the loop diuretic alone or in combination with the mast cell degranulator is from about 1 to 50 µg/cm$^2$/hr.

14. The method of claim 13 wherein the maximum flux of the loop diuretic alone or in combination with the mast cell degranulator is from about 5 to 25 µg/cm$^2$/hr.

15. The method of claim 4 wherein the maximum flux of the glucocorticosteroid is from about 0.005 to 5 µg/cm$^2$/hr.

16. The method of claim 15 wherein the maximum flux of the glucocorticosteroid is from about 0.1 to 1.0 µg/cm$^2$/hr.

17. The method of claim 1 comprising administering to the warm-blooded animal an amount of said adverse skin reaction preventing or treating agent sufficient to treat or prevent allergic contact dermatitis caused by a skin-sensitizing agent in the form of a gel, said amount of the loop diuretic being from about 0.1 to 10% by weight, the amount of the mast cell degranulator being from about 0 to 20% by weight and the amount of the glucocorticosteroid being from about 0 to 5% by weight.

18. The method of claim 17 wherein the amount of the loop diuretic is from about 0.25 to 2.0% by weight, the amount of the mast cell degranulator is from about 1 to 10% by weight.

19. The method of claim 1 comprising administering to the warm-blooded animal an amount of said adverse skin reaction preventing or treating agent sufficient to treat or prevent allergic contact dermatitis caused by a skin-sensitizing agent in the form of a gel, said amount of the loop diuretic being from about 0.1 to 2.0% by weight, the amount of the mast cell degranulator being from about 0 to 20% by weight and the amount of the glucocorticosteroid being from about 0 to 5% by weight.

20. The method of claim 19 wherein the amount of the loop diuretic is from about 0.25 to 1.0% by weight, the amount of the mast cell degranulator is from about 2.0 to 10% by weight and the amount of the glucocorticosteroid is from about 0.5 to 2.0% by weight.

21. A transdermal delivery system for transdermally administering to a warm-blooded animal an amount of an adverse skin reaction preventing or treating agent sufficient to prevent or treat said adverse reaction without achieving a systemically active concentration, said adverse skin reaction preventing or treating agent comprising a loop diuretic alone or in combination with at least one mast cell degranulator or at least one glucocorticosteroid, said system comprising:

(a) a first transdermal device comprising a matrix for placing the adverse skin reaction preventing or treating agent in transmitting relationship to the skin; and (b) a second transdermal device comprising a matrix for placing a therapeutic agent in transmitting relationship to the skin after the adverse skin reaction preventing or treating agent has been transdermally administered to the skin from the first transdermal device.

22. The transdermal delivery system of claim 21 wherein the first and second transdermal devices are contained within a single transdermal patch.

23. A method of transdermally administering to a warm-blooded animal a therapeutic agent without thereby eliciting an adverse reaction from the skin comprising transdermally administering before, after or during the administration of the therapeutic agent an amount of an adverse skin reaction preventing agent sufficient to prevent said adverse reaction without achieving a systemically active concentration, said adverse skin reaction preventing agent comprising a loop diuretic alone or in combination with at least one mast cell degranulator or at least one glucocorticosteroid to said warm-blooded animal.

24. The method of claim 23 wherein the loop diuretic is selected from the group consisting of ethacrynic acid, furosemide and bumetanide.

25. The method of claim 23 wherein the mast cell degranulator is selected from the group consisting of cis-urocanic acid, 1-furanacrylic acid, 2-pyrole acrylic acid, 2-thiophenacrylic acid, dihydrourocanic acid, trans-urocanic acid, histamine, $N^1$-methylhistamine, $N^1$-methylhistidine, histidine, imidazolepyruvic acid, $N^3$-methylhistidine, imidazoleacetic acid, hydantoin 5-propionic acid, imidazolonepropionic acid, psoralen treated with ultraviolet radiation, chloroquine, histamine, capsaicin, morphine sulfate, a sodium channel ionophore, a calcium channel ionophore, an inhibitor of Na+/K+ channel ATPase, quinine, 4-amino pyridine, anti-human IgE antibody, substance P, estradiol, somatastatin, carbachol, progesterone, spantide, and clonidine.

26. The method of claim 25 wherein the analogs of cis-urocanic acid are selected from the group consisting of 1-furanacrylic acid, 2-pyrole acrylic acid, 2-thiophenacrylic acid, dihydrourocanic acid and trans-urocanic acid.

27. The method of claim 23 wherein the glucocorticosteroid is selected from the group consisting of hydrocortisone, beclomethasone, betamethasone, clobetasol, desonide, dexamethasone, fluocinonide, prednisone, and triamcinolone.

* * * * *